US006054034A

United States Patent [19]
Soane et al.

[11] Patent Number: 6,054,034
[45] Date of Patent: Apr. 25, 2000

[54] ACRYLIC MICROCHANNELS AND THEIR USE IN ELECTROPHORETIC APPLICATIONS

[75] Inventors: David S. Soane; Zoya M. Soane, both of Piedmont; Herbert H. Hooper, Belmont; M. Goretty Alonso Amigo, Santa Clara, all of Calif.

[73] Assignee: ACLARA Biosciences, Inc., Mountain View, Calif.

[21] Appl. No.: 08/853,661

[22] Filed: May 9, 1997

Related U.S. Application Data

[63] Continuation-in-part of application No. 08/832,790, Apr. 4, 1997, which is a continuation-in-part of application No. 08/627,484, Apr. 4, 1996, Pat. No. 5,858,188, which is a continuation-in-part of application No. 08/430,134, Apr. 26, 1995, abandoned, which is a continuation of application No. 08/196,763, Feb. 14, 1994, abandoned, which is a continuation of application No. 07/880,187, May 7, 1992, abandoned, which is a continuation of application No. 07/487,021, Feb. 28, 1990, Pat. No. 5,126,022.

[51] Int. Cl.$^7$ ..................................................... G01N 27/26
[52] U.S. Cl. ...................... 204/601; 204/451; 435/287.2; 435/288.5; 422/68.1; 156/291; 156/273.5
[58] Field of Search ................................... 204/451, 455, 204/601, 605; 435/287.2, 288.5; 422/100, 68.1; 210/198.2, 198.3, 656, 658; 428/36.9, 36.92; 156/291, 273.5

[56] References Cited

U.S. PATENT DOCUMENTS

| | | |
|---|---|---|
| 4,334,234 | 6/1982 | Shirato et al. . |
| 4,509,063 | 4/1985 | Sugitani et al. . |
| 4,558,333 | 12/1985 | Sugitani et al. . |
| 4,570,167 | 2/1986 | Sugitani et al. . |
| 4,690,749 | 9/1987 | Van Alstine et al. . |
| 4,705,616 | 11/1987 | Andresen et al. ...................... 204/299 |
| 4,708,782 | 11/1987 | Andresen et al. ...................... 204/299 |
| 4,801,201 | 1/1989 | Eichweber .................................. 356/4 |
| 4,891,120 | 1/1990 | Sethi et al. .......................... 204/299 R |
| 4,898,658 | 2/1990 | Karger et al. ............................ 204/299 |
| 4,908,112 | 3/1990 | Pace ..................... 204/299 R |
| 4,970,532 | 11/1990 | Komuro et al. . |
| 5,082,559 | 1/1992 | Eguchi et al. ........................... 210/198 |
| 5,114,768 | 5/1992 | Swedberg . |
| 5,126,022 | 6/1992 | Soane et al. . |
| 5,433,898 | 7/1995 | Thakrar et al. .......................... 264/1.7 |
| 5,484,823 | 1/1996 | Noguchi et al. . |
| 5,500,071 | 3/1996 | Kaltenbach et al. ................. 156/272.8 |
| 5,528,272 | 6/1996 | Quinn et al. . |
| 5,545,280 | 8/1996 | Wenz . |
| 5,571,410 | 11/1996 | Swedberg et al. ................... 210/198.2 |
| 5,858,188 | 1/1999 | Soane et al. . |

FOREIGN PATENT DOCUMENTS

| | | |
|---|---|---|
| 0 452 055 B1 | 10/1991 | European Pat. Off. . |
| 0 665 430 A1 | 6/1995 | European Pat. Off. . |
| 5-264502 | 10/1993 | Japan . |
| WO94/29400 | 12/1994 | WIPO . |

OTHER PUBLICATIONS

Hjerten, "High–Performance Electrophoresis Elimination of Electroendosmosis and Solute Adsorption," *J. Chrom.* (1995), pp. 191–198.

Lin et al., "Polymeric Hollow Fibers for Capillary Electrophoresis," *J. Micro.* (1995), pp. 245–253.

Nielen et al., "Capillary Zone Electrophoresis Using a Hollow Polypropylene Fiber," *J. High Res. Chrom.* (1983), pp. 62–64.

Schutzner et al., "Electrophoresis in Synthetic Organic Polymer Capillaries: Variation of Electroosmotic Velocity and Potential with pH and Solvent Composition," *Anal. Chem*, (1922), vol. 64, No. 17.

Ratner, "Surface modification of polymers: chemical, biological and surface analytical challenges," *Biosensors & Bioelectronis*, (1995) 10, pp. 797–804.

Cobb et al., "Electrophoretic Separations of Proteins in Capillaries with Hydrolytically Stable Surface Structures," *Anal. Chem.* (1990), pp. 2478–2483.

Gilges et al., "Capillary Zone Electrophoresis Separations of Basic and Acidic Proteins Using Poly(vinly alcohol) Coatings in Fused Silica Capillaries," *Analytical Chem.* (1994), pp. 2038–2046.

Rohlicek, et al., "Determination of the isoelectric point of the capillary wall in capillary electrophoresis Application to plastic capillaries," *J. Chrom.* (1994), pp. 369–373.

*Primary Examiner*—William H. Beisner
*Attorney, Agent, or Firm*—Bertram I. Rowland; Rae–Venter Law Group, P.C.

[57] ABSTRACT

Microchannels having at least an acrylic inner surface and methods of their use in electrophoretic applications are provided. The subject microchannels may be in the form of a variety of configurations suitable for holding an electrophoretic medium. The subject microchannels give rise to substantially reduced EOF and/or adsorption as compared to fused silica under conditions of electrophoresis and find use in a variety of electrophoretic applications in which charged entities are moved through a medium under the influence of the an applied electric field.

7 Claims, 5 Drawing Sheets

ACRYLIC MICROCHANNELS AND THEIR USE IN ELECTROPHORETIC APPLICATIONS

CROSS REFERENCE TO RELATED APPLICATIONS

This application is a continuation-in-part of application Ser. No. 08/832,790, filed Apr. 4, 1997, which application is a continuation-in-part of application Ser. No. 08/627,484, filed Apr. 4, 1996, now U.S. Pat. No. 5,858,188, which application is a continuation-in-part of application Ser. No. 08/430,134, filed Apr. 26, 1995, now abandoned, which application is a continuation of application Ser. No. 08/196,763, filed Feb. 14, 1994, now abandoned, which application is a continuation of application Ser. No. 07/880,187, filed May 7, 1992, now abandoned, which application is a continuation of application Ser. No. 07/487,021, filed Feb. 28, 1990, now U.S. Pat. No. 5,126,022, the disclosures of which are incorporated by reference herein.

INTRODUCTION

1. Field of the Invention

The field of this invention is electrophoresis.

2. Background of the Invention

Electrophoresis has become an indispensable tool of the biotechnology industry, as it is used extensively in the separation, identification and preparation of pure samples of nucleic acids, proteins and carbohydrates. For example, electrophoresis is critical to DNA sequencing applications such as the Maxam-Gilbert and Sanger dideoxy methods, where a major step of these methods is the electrophoretic separation of labeled DNA fragments.

Of increasing interest in the field of electrophoresis is the use of devices having micro cross-sectional dimensions, such as microbore capillaries and microchannels. Use of devices in which the electrophoretic medium is housed in a container having micro cross-sectional dimensions can provide a number of different advantages over conventional slab gel electrophoretic configurations. For example, in capillary electrophoresis (CE) where electrophoresis is carried out in microbore capillaries, one is able to achieve separation and resolution of sample components much quicker than with conventional slab gel configurations. Microchannel electrophoresis (MCE), in which electrophoresis is carried out in micro channels on a planar substrate also provides for shorter run times than is achievable with conventional slab gels. In addition, with microchannels the possibility exists to obtain high throughput applications, where the overall number of samples run per minute is greatly increased. Because much shorter run times are required in CE and MCE, CE and MCE are particularly attractive methods for projects requiring the separation and resolution of complex mixtures of large numbers of differently sized nucleic acids, such as the Human Genome Project.

Traditionally, the material of choice for use in applications such as CE and MCE has been fused silica. Despite the popularity of fused silica as a material for use in electrophoretic applications, fused silica has many shortcomings. The internal surface of a fused silica microchannel, e.g. capillary, under conditions of electrophoresis is negatively charged. This negative charge gives rise to the phenomenon known as electroosmotic flow (EOF) which modulates the flow characteristics of, and therefore affects the separation of, individual sample components in the separation media present in the microvessel. Furthermore, sample components such as proteins and other analytes can adsorb to the negatively charged surface of the fused silica and thereby unpredictably disrupt the uniformity of the EOF, thereby contributing to the irreproducibility of the results obtained in the electrophoretic application.

To overcome the above problems, various treatments have been developed, including dynamic and covalent modification of the internal surface of fused silica microvessels. See U.S. Pat. No. 5,221,447 for examples of surface modification of fused silica capillaries. Although under ideal circumstances these treatments can reduce or even eliminate the problems associated with EOF and solute adsorption, in practice these treatments can fail to completely mask the negatively charged silica surface. Furthermore, the modified layer on the surface resulting from such treatments may not be entirely stable under the conditions of electrophoresis. Finally, surface modified fused silica microvessels such as capillaries are difficult to manufacture, as the manufacturing process can be laborious and time consuming.

Accordingly, there has been interest in the identification of alternative materials to fused silica from which media containment means, i.e. microchannels, suitable for use in electrophoresis may be fabricated, where good separation and resolution of sample components can be achieved without surface modification of the material. Ideally, such materials would give rise to substantially reduced EOF and/or sample component adsorption as compared with untreated fused silica under electrophoretic conditions. Furthermore, such materials should be moldable, optically transparent for on-line detection, and stable under conditions of electrophoresis.

Relevant Literature

Capillary Electrophoresis is reviewed in Barron & Blanch, Separation and Purification Methods, (1995) 24:1–118;

A variety of methods for controlling electroosmotic flow in fused silica capillaries have been reported, including: (1) manipulation of radial electric fields, Lee et al., Anal. Chem. (1990) 62:1550–1552; Lee et al., Anal. Chem. (1991) 63:1519–1528; Lee et al., J. Chromatogr. (1991) 559:133–140; (2) chemical modification of the fused silica surface, see Belder & Schomburg, J. High Res. Chromatogr. (1992) 15:686:693; Vanderhoff et al., Separation and Purification Meth. (1977) 6:61–87; Hjerten, J. Chromatogr. (1985) 347:191–198; Lux et al., J. High Res. Chromatogr. (1990) 13:145–148; and (3) adjustment of electrophoretic medium characteristics, see Lukacs & Jorgenson, J. High Res. Chromatogr. Comm. (1985) 8:407–411; Schwer & Kendler, Anal. Chem. (1991) 63:1801–1807.

SUMMARY OF THE INVENTION

Microchannels comprising at least an acrylic inner surface and their use in electrophoretic applications are provided. The microchannels of the subject invention have a variety of different configurations and have micro scale inner cross-sectional dimensions. The acrylic inner surface of the subject microchannels gives rise to substantially reduced EOF and/or adsorption under conditions of electrophoresis, as compared to native fused silica, making the subject microchannels particularly suited for use in a number of different electrophoretic applications.

DESCRIPTION OF THE SPECIFIC EMBODIMENTS

Figure 1:
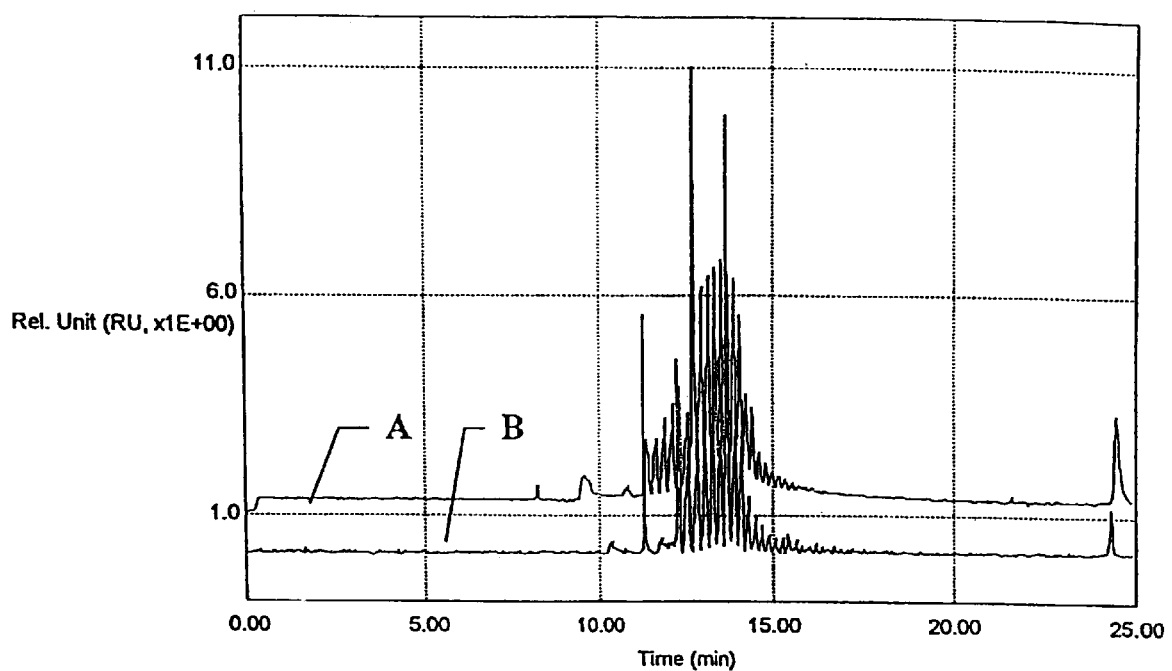
FIG. 1 provides results of electrophoretic separation of a 10 base pair DNA ladder in an untreated polymethylmethacrylate capillary and a coated fused silica capillary.

Microchannels having at least an acrylic inner surface and their use in electrophoretic applications are provided. The microchannels have a variety of cross-sectional configurations, where the channels have micro scale cross-sectional inner dimensions. The subject microchannels give rise to substantially reduced EOF and/or sample component adsorption under conditions of electrophoresis, as compared with native or untreated fused silica, and are therefore suited for a variety of different electrophoretic applications.

The microchannels of the subject invention may be open or closed, where by "open" is meant that the internal volume of the microchannel is not completely separated on at least one longitudinal side from the external environment, while by "closed" is meant that the internal volume of the channel is completely separated longitudinally from the external environment. Examples of open microchannels include troughs, trenches and the like, while closed channels are exemplified by cylinders, tubes, capillaries and the like. The subject microchannels will have microscale cross-sectional inner dimensions, such that the inner cross-sectional inner dimensions of the microchannels will be greater than 1 $\mu$m and less than 1000 $\mu$m. Generally, the cross-sectional inner dimension(s) of the microchannel, i.e. width, depth or diameter depending on the particular nature of the channel, will generally range from about 1 to 200 $\mu$m, usually from about 10 to 150 $\mu$m, more usually from about 20 to 100 $\mu$m, with the total inner cross sectional area of the microchannel ranging from about 100 to 40000 $\mu$m$^2$, usually from about 400 to 25,000 $\mu$m$^2$. The inner cross-sectional shape of the microchannel may vary among a number of different configurations, including rectangular, square, rhombic, triangular or V-shaped, circular, semicircular, ellipsoid and the like. The length of the microchannel will necessarily depend on the specific nature of the vessel as well as the electrophoretic device in which it is to be employed. For example, where the microchannel is a trough or trench in a substrate, the length of the microchannel may range from about 0.1 to 100 cm, and will generally range from about 1 to 20 cm, usually from about 1 to 10 cm, and more usually from about 5 to 10 cm, while for capillaries the length will generally range from about 10 to 100 cm, usually from about 10 to 75 cm, more usually from about 20 to 50 cm. Where the subject microvessel is contained within a capillary, the thickness of the wall of the capillary may range from about 50 to 1000 $\mu$m, usually from about 100 to 500 $\mu$m, more usually from 100 to 150 $\mu$m, to provide a capillary with an outer diameter ranging from 100 to 2000 $\mu$m, usually from about 150 to 400 $\mu$m.

In the subject movement area or microchannels, at least the inner surface defining the microchannel will be an acrylic polymer material. By "at least the inner surface" is meant that anywhere from a portion to the entire wall(s) of the microchannel may be an acrylic polymer material, where when only a portion of the microchannel is an acrylic polymer material, that portion will be the inner portion of the channel wall that is immediately adjacent to the electrophoretic medium present in the channel during electrophoresis. Thus, the entire microchannel may be fabricated from the acrylic polymer material, or the inner surface of the microchannel may be coated with a thin acrylic polymer layer. Generally, the thickness of the acrylic portion of the microchannel will be at least about 1 $\mu$m, usually at least about 10 $\mu$m, more usually at least about 25 $\mu$m, and may be several mm or higher, but will usually not exceed 10 mm, and more usually will not exceed 5 mm.

Where only the inner portion defining the microchannel is an acrylic polymer material, the remainder of the channel wall may be any convenient material, including a heat dissipating material which serves to absorb heat produced in the electrophoretic medium during electrophoresis. Thus, where the microchannel is on the surface of an acrylic substrate, e.g. a trench or trough, the substrate may be a composite substrate comprising a layer of acrylic polymer over a heat dissipating material. For capillaries, the acrylic inner surface, i.e. inner tubular section, of the capillary may be surrounded or coated with a layer or outer tubular section of heat dissipating material, where the outer layer or coating of absorbent material may be partially removed as necessary to expose the inner acrylic portion of the capillary wall when on-line detection is desired. Specific materials which provide for heat dissipation and may make up at least a portion of the microchannels include glasses, ceramics, metals and the like. Specific heat absorbent materials of interest, depending on the nature of the microchannel, include aluminum, copper, glass and the like. In use, the metals would be removed or insulated from contact with any conductive mediums to prevent a short circuit.

As mentioned above, microchannels according to the subject invention have a variety of different configurations, including trenches or troughs on or at the surface of a substrate, capillaries, and other microscale configurations suitable for holding or containing an electrophoretic medium during electrophoresis. Where the microchannel is a trench or trough extending downward from the surface of a substrate, conveniently a groove in the substrate, the substrate may be square, rectangular, circular and the like, and will have dimensions which will vary considerably depending on the intended use of the microchannel, with a card-like or substantially regular parallelepiped dimensioned substrate being of particular interest. Where the substrate has card-like or substantially regular parallelepiped dimensions, the length of the substrate will typically range from about 2 to 200 mm, the width of the substrate will typically range from about 2 to 200 mm, while the thickness of the substrate will typically range from about 0.1 to 10 mm. One or more, usually at least 2 and up to 100 or more, microchannels may be present on or at the surface of the substrate, where when a plurality of microchannels are present at the substrate surface, the possibility exists to have a number of different electrophoretic applications running at the same time on a single substrate. The microchannel(s) present on the substrate surface can be linear, branched or in some other convenient configuration. With branched microchannels or trenches, the possibility exists to have a first trench or channel intersected by one or more side channels, where the side channels may intersect the main channel at any convenient angle.

As the microchannel(s) present on the substrate surface may be open, it may be desirable to separate the internal volume of the channel, and thereby the medium housed in the channel, from the external environment. In such instances a cover can be employed, which may take the form of a cover plate or a film cover. The cover rests upon, or is adhered to, the surface of the substrate and thereby separates the internal volume of the channel from the environment. The cover may be fabricated from one material, which may be coated on the side facing the microchannel, or as a composite of materials, such as laminated composite. Suitable materials for the cover include, for example, fused silica and polymeric materials such as acrylic polymers, and films of polymers such as polyethylene terephthalate (PET; e.g., Mylar™), and polyethylene (PE). Any of various adhesives may be used; for example, polyethylene film or glass may be coated with an elastomeric adhesive such as polydimethylsiloxane (PDMS), and the adhesive layer then forms an inner surface of the microchannel. Where necessary, one or more of the cover plate surfaces may be treated to reduce any EOF that may arise during electrophoresis. The necessity for treatment, as well as the specific type of treatment, will necessarily depend on the particular material employed as the cover plate. For example, where the cover plate is fabricated from an acrylic polymer material, where the material may be the same or different from the acrylic polymer material present on at least the inner surface of the channel, it will generally be unnecessary to treat the surface of the plate. However, where the cover plate is fabricated from a material which has charged surfaces under conditions of electrophoresis, such as fused silica, it will generally be necessary to treat at least the surface in contact with the medium in the channel to reduce the presence of EOF during electrophoresis. A number of different methods are known which reduce or eliminate EOF. See references discussing the surface modification of fused silica materials listed in the Relevant Literature supra. As with the substrate, the coverplate may be fabricated from a single type of material or be a composite of one or more, usually two, materials. Where the cover plate is a composite of two or more materials, the first material or layer, i.e. the layer in contact with the medium in the channel, will generally be an acrylic polymeric material, treated fused silica and the like, while the second material or layer, as well as any subsequent layers, may be any convenient material, such as the heat dissipating materials described above.

The thickness of a cover plate will usually range from about 0.01 to 10 mm, more usually from about 0.1 to 1.0 mm. Thickness of a cover film will usually range from about 1 mil to 5 mils (about 0.025 to 0.125 mm), more usually from about 1 mil to 2 mils (about 0.025 to 0.050 mm). The length and width of the cover plate may be similar to, or different from, the length and width of the substrate, but will usually be substantially the same as those of the substrate. The cover plate may have substantially smooth, planar, flat surfaces, or optionally may be a mirror image of the substrate. Although not necessary, the cover plate will generally be sealed to the substrate. The cover plate and substrate may be sealed using any convenient means, such as ultrasonic welding, pressure, thermoprocessing, adhesives, sealants, physical conformance and the like.

The polymer material (which may be an acrylic polymer material) present on at least the inner surface of the microchannels will be water insoluble, solid, non-porous and electrically non-conductive, i.e. it will have a high electrical resistance. As the polymer material is non-porous, the material will be impermeable to both small and large molecules, such as water, charged ions and the like. The polymer material will be stable under the conditions of capillary electrophoresis, i.e. aqueous conditions having high salt concentrations in which the pH may range from 2 to 12. Where the polymer material is a block material or capillary, it will be suitable for precision forming or shaping using molding and extrusion processes, and have sufficient mechanical strength and rigidity to retain its shape under the conditions of electrophoresis. Importantly, the polymer material will be optically transparent, generally allowing light of wavelengths ranging from 180 to 1500 nm, usually 220 to 800 nm, more usually 250 to 800 nm, to have low transmission losses. The polymer material should be sufficiently free of additives or impurities which would interfere with the electrophoresis and the desired optical characteristics of the microchannel prepared from it, such as transparency at a particular wavelength range.

The acrylic polymer material may comprise one or more, usually not more than four, more usually not more than three, distinct acrylic polymers, where the polymers may be polymerized from a variety of one or more acrylic monomers, where the term acrylic includes both methacrylic and acrylic. The acrylic homo and co-polymers from which microchannels are prepared will be uncrosslinked or crosslinked.

Where acrylic copolymers are present in the polymer material, the opportunity exists to polymerize the copolymers from two or more distinct monomers, where each monomer imparts a different characteristic to the resultant copolymer material. In this situation, consideration will be given to the following criteria: (a) the desired surface properties of the polymer, e.g. its propensity to cause EOF and/or adsorb solutes under electrophoretic conditions, (b) the desired mechanical properties of the polymer material comprising the copolymer, such as strength and rigidity; (c) the desired optical properties of the polymer material, such as transparency at a particular wavelength range; and (d) the desired wettability of the polymer material. For example, to obtain a polymer material that is capable of being extruded into a capillary suitable for electrophoresis, hydrophobic monomers which impart mechanical rigidity to the material may be copolymerized with hydrophilic monomers that impart wettability to the material. Hydrophobic monomers of interest for copolymerization include those acrylic hydrophobic monomers having neutral ester substituents, usually alkyl substituents of from 1 to 18 carbon atoms, more usually 1 to 10 carbon atoms. Hydrophilic monomers which may be copolymerized with the hydrophilic monomers include acrylic acids and esters, where the ester substituent is usually 1 to 5 carbon atoms in length, more usually 2 to 4 carbon atoms, with usually at least one oxygen atom. For such copolymers, the ratio of hydrophilic to hydrophobic monomeric units in the copolymer formulation will generally range from 0.01 to 1.00:1, usually from 0.01 to 0.50:1, more usually from 0.01 to 0.30:1. Acrylic copolymers from which the subject microchannels are prepared may be random or block copolymers.

For the most part, the polymer materials from which the subject microchannels are prepared will be polymerized from one or more different monomers, wherein individual monomeric units along the chain may vary, depending upon whether the polymer is a homo- or copolymer, as well as whether the polymer is random or block, where the monomers will for the most part be of the formula:

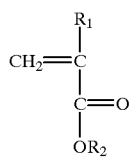

wherein $R_1$ is H or $CH_3$;

and $R_2$ is the same as or different from $R_1$, being H, $CH_3$ or a non-aromatic alkyl group of from 2 to 18 carbon atoms, usually 2 to 10 carbon atoms, where the alkyl group may be linear, branched or cyclic, may have one or more heteroatoms, usually not more than 2, and may have one or more sites of unsaturation, usually not more than 2, where the alkyl group may be a halocarbon comprising one or more halogen atoms, usually fluorine atoms, up to perhalo;

wherein the total number of monomeric units in the polymer is sufficient to provide for a polymer having a molecular weight ranging from about $10^2$ to $10^4$ kdal, usually from about $10^3$ to $5 \times 10^3$ kDal.

Of interest are acrylic polymers polymerized from one or more of the following monomers: methyl acrylate, methyl methacrylate, ethyl acrylate, ethyl methacrylate, isopropyl acrylate, isopropyl methacrylate, t-butyl acrylate, t-butyl methacrylate, trifluoroethyl acrylate, trifluoroethyl methacrylate, isobornyl acrylate, isobornyl methacrylate, adamantyl acrylate, adamantyl methacrylate, acrylic acid, methacrylic acid, glycerol acrylate, glycerol methacrylate, hydroxyethyl methacrylate, ethoxyethyl methacrylate, cyclohexyl acrylate, cyclohexyl methacrylate, tetradyrofurfuryl acrylate, tetradyrofurfuryl methacrylate, 2-ethoxyethyl acrylate, 2-ethoxyethyl methacrylate, 2-methoxyethyl acrylate, 2-methoxyethyl methacrylate, and the like.

Where the microchannel is fabricated from a crosslinked acrylic polymer, the polymer may be polymerized from one or more of the above monofunctional monomers and one or more bifunctional or multifunctional acrylic monomers that provide for crosslinking. Bi- or multifunctional acrylic monomers that provide for crosslinking will for the most part be described by the formula:

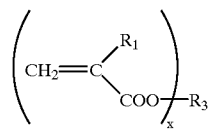

wherein $R_1$ is the same as above;

$R_3$ is a non-aromatic, linear, branched or cyclic saturated alkyl group of from 2 to 10 carbon atoms which may comprise 1 or more heteroatoms, usually not more than 3, usually oxygen; and x is an integer from 2 to 4.

Specific acrylic monomers of interest that are at least bifunctional include ethylene glycol dimethacrylate, ethylene glycol diacrylate, neopentyl glycol dimethacryalate, neopentyl glycol acrylate, diethoxylated trimethylolpropane triacrylate, and the like.

Of particular interest are microchannels wherein the acrylic portion is a homopolymer polymerized from acrylic or methacrylic esters, wherein the ester substituent contains 1 to 10 carbon atoms, usually 1 to 2 carbon atoms, with polymethylmethacrylate (PMMA) being preferred.

The subject polymers may be obtained commercially, or readily prepared using known methods.

The subject microchannels can be prepared using conventional techniques known in the art, such as thermomolding, extrusion, cast molding and the like.

The subject microchannels find use in a variety of electrophoretic applications, where by "electrophoretic applications" is meant an application where charged entities, e.g. molecules, particles and the like, are moved through a medium in response to a voltage gradient being applied across the medium. In using the subject microchannels in electrophoretic applications, the particular method employed will depend at least partially on the nature of the electrophoretic device in which the subject microchannels are employed, as well as the nature of the application to be performed. Generally, the first step will be to fill the inner volume of the microchannel with a suitable electrophoretic medium. Depending on the particular electrophoretic application to be run, electrophoretic media which find use include aqueous and non-aqueous solutions, dispersions and gels, where various buffers, organic and inorganic modifiers, and the like, may be present in the media.

The next step will generally be the introduction of the charged entities to be moved during the electrophoretic application into the medium. Introduction may be achieved using any convenient means, including electrokinetic injection, hydrodynamic injection and the like, where the particular means employed will, for the most part, depend on the configuration of the channel as well as the necessity to introduce a precise volume of sample. For example, with channels in a capillary, means of sample introduction may include electrokinetic injection, hydrodynamic injection, spontaneous fluid displacement and the like, as described in Barron & Blach, supra, at §§ 6.5.2–6.5.4. For MCE applications in which the electrophoretic application is carried out in a microchannel on a substrate, where the microchannel configuration employed comprises a second channel intersecting a first or main channel, the second channel can be filled with sample followed by movement of the volume or plug of sample in the intersection of the second and main channels into the main channel through application of an appropriate electric field. The introduced charged entities may be components of a complex mixture or sample, reagents, and the like, depending on the particular application to be performed.

Following introduction of the to be manipulated charged entities, an electric field or fields will be applied to the medium. Depending on the particular application, the voltage gradient applied to the medium may range anywhere from 10 to 1000 V/cm, usually from 50 to 500 V/cm. Through modulation of the applied electric field or fields, the movement of the charged entities through the medium may be manipulated as desired, depending on the particular application.

For electrophoretic separation applications, the electrophoretic medium introduced into the internal volume of the microchannel will be a separation matrix. Separation media or matrices which find use in electrophoretic separation applications may comprise buffers and other additives, as well as polymeric agents, where both crosslinked and uncrosslinked linear polymers of both synthetic and natural origin, etc., may find use. Separation matrices that find particular use in the separation of nucleic acids are reviewed in Barron & Blanch, Separation and Purification Methods (1995) 24:1–105, § 6.8, specifically incorporated herein by reference. Where necessary, the separation matrix may be loaded into the internal volume of the channel under a pressure differential.

For electrophoretic separation applications, after the microchannel is placed in the device and is ready for electrophoresis, the sample to be electrophoresed will be introduced into the microchannel. Of particular interest are sample introduction techniques which provide for the accurate and efficient delivery of a sample volume to the electrophoretic media. The sample volume will be sufficiently small to avoid band broadening during electrophoresis. To avoid significant band broadening, the sample volume will generally range from about 1 picoliter to 1 microliter. Methods which provide for the introduction of precise sample volumes, particularly in CE, include electrokinetic injection, hydrodynamic injection, spontaneous fluid displacement and the like, as described in Barron & Blach, supra, at §§ 6.5.2–6.5.4. For MCE, of particular interest is the use of intersecting channels, where the sample volume or plug at the intersection of a secondary and main channel is moved into the main channel as a result of an applied electric field, as described above.

Following sample introduction, a voltage gradient will be applied to the separation media, causing the various sample components to migrate through the media at rates proportional to their particular charge and/or mass. Any convenient means for applying a voltage gradient across the medium may be employed.

The separated and resolved components are then detected using any convenient detection means. The detection system employed will depend on the particular signal being used as an indication of the separated component, e.g. UV absorbance detectors where UV absorption is the signal, fluorescence detectors where laser induced fluorescence (LIF) is the signal, and the like.

The subject microchannels are suitable for use in the electrophoretic separation of the components of a variety of samples, including complex mixtures of proteins, carbohydrates and nucleic acids. Of particular interest is the use of the subject microchannels in the electrophoretic separation of complex mixtures of large numbers of differently sized nucleic acids, such as DNA fragments generated in large genome sequencing applications. Of particular interest is the separation of DNA fragments ranging in size from about 10 to 10,000,000 bp, usually from about 10 to 10,000 bp, more usually from about 10 to 5,000 bp. DNA detection and sequencing methods employing microchannels such as capillaries are extensively described in Barron & Blach, supra, § 6.6 and Lipshutz & Fodor, Curr. Opinion in Struct. Biol. (1994) 4: 376–380. The subject microchannels are particularly suited for such applications as they give rise to substantially reduced EOF and sample component adsorption as compared to native or untreated fused silica. By substantially reduced EOF is meant that the EOF occurring in the subject microchannels under electrophoretic conditions is generally less than about 50%, usually less than about 40%, more usually less than about 30% of the EOF present in native or untreated fused silica microchannels under similar conditions. In the subject microchannels, generally less than 20%, usually less than 15%, more usually less than 10% of the overall electrophoretic mobility of the charged entities moving through the channel under an applied voltage gradient will be attributable to EOF.

In addition to the subject microchannels and methods of their use in electrophoresis, kits are provided comprising the subject microchannels with an electrophoretic medium, e.g. separation matrix, where the medium may be preloaded in the channel or separate from the channel. The kits may further comprise various detectable labels capable of providing a signal, usually fluorescence, which may be combined with a sample and provide for a detectable signal during or after electrophoresis, such as labeled nucleic acids, e.g. fluorescently labeled oligonucleotide primers, fluorescently labeled ddNTPs, and the like.

The following examples are offered by way of illustration and not by way of limitation.

EXPERIMENTAL

Example 1.

CE of dsDNA in Polymethylmethacrylate Capillaries

A 34 cm polymethylmethacrylate (PMMA) capillary (Biogeneral, Inc.) having an inner diameter of 75 $\mu$m and an outer diameter of 375 $\mu$m was pressure-loaded with a separation media prepared from 0.4 g of hydroxyethylcellulose (HEC) (MW 90,000–105,000) and 1.5 g of hydroxypropylcellulose (HPC) (MW 300,000) dissolved in 98.1 g of 0.5× TBE at 400 psi. A 10 base pair DNA ladder consisting of about 30 10-bp repeats (GibcoBRL) was loaded electrokinetically for five seconds at 5 kV. Electrophoresis was performed at 5 kV using a prototype electrophoresis instrument with a confocal fluorescence detector having Spindler & Hoyer (Medford, Mass.) optical components and an Omnichrome Argon Ion Laser operating at about 12 mW and 488 nm.

The results are provided in FIG. 1. Trace A is the separation of the 10 base pair ladder in a polymethylmethacrylate capillary, while trace B is the separation of an identical sample in a coated fused silica capillary of similar dimensions. Trace "A" has a positive baseline offset for comparison purposes only. Injection of a neutral marker was not detected within one hour of injection, indicating a negligible electroosmotic flow in both the polymethylmethacrylate and coated fused silica capillaries. The tallest peak in each separation corresponds to the 100 base-pair fragment. Since any electroosmotic mobility would oppose the migration of the sample species toward the detector during the run, little electroosmosis was indicated by both the similarity and short run times of the two runs. Separations of an analogous sample in a bare fused silica capillary under similar conditions were of significantly poor quality and exhibited a reverse elution order.

Example 2

CE of Single Stranded DNA Ladder in Polymethylmathacrylate Capillary

A 10 cm length of polymethylmethacrylate (PMMA) capillary (Biogeneral, Inc.) having an inner diameter of 75 $\mu$m was loaded with sieving buffer containing 2% (by wt) hydroxyethylcellulose (HEC, MW 90,000–105,000), 6M urea, 10% formamide, and 1× TBE. The capillary was placed into a horizontal capillary holder in a capillary electrophoresis unit. DNA was injected eletrokinetically at 150 V/cm for 15 seconds. For the DNA sample, TAMRA (N,N,N',N'-tetramethyl-6-carboxyrhodamine) labelled GeneScan 500 ladder (Perkin Elmer) was used. GeneScan 500 ladder consists of 16 fragments of 500, 490, 450, 400, 350, 340, 300, 250, 200, 160, 150, 139, 100, 75, 50 and 35 bases. Electrophoresis was performed at 150 V/cm for 20 minutes, with sieving buffer in the anodic reservoir. Detection was performed using confocal fluorescence detection. Separated fragments of DNA were detected by excitation of TAMRA with a xenon lamp (440–490 nm), with emission light collected at 520 nm.

Figure 2:
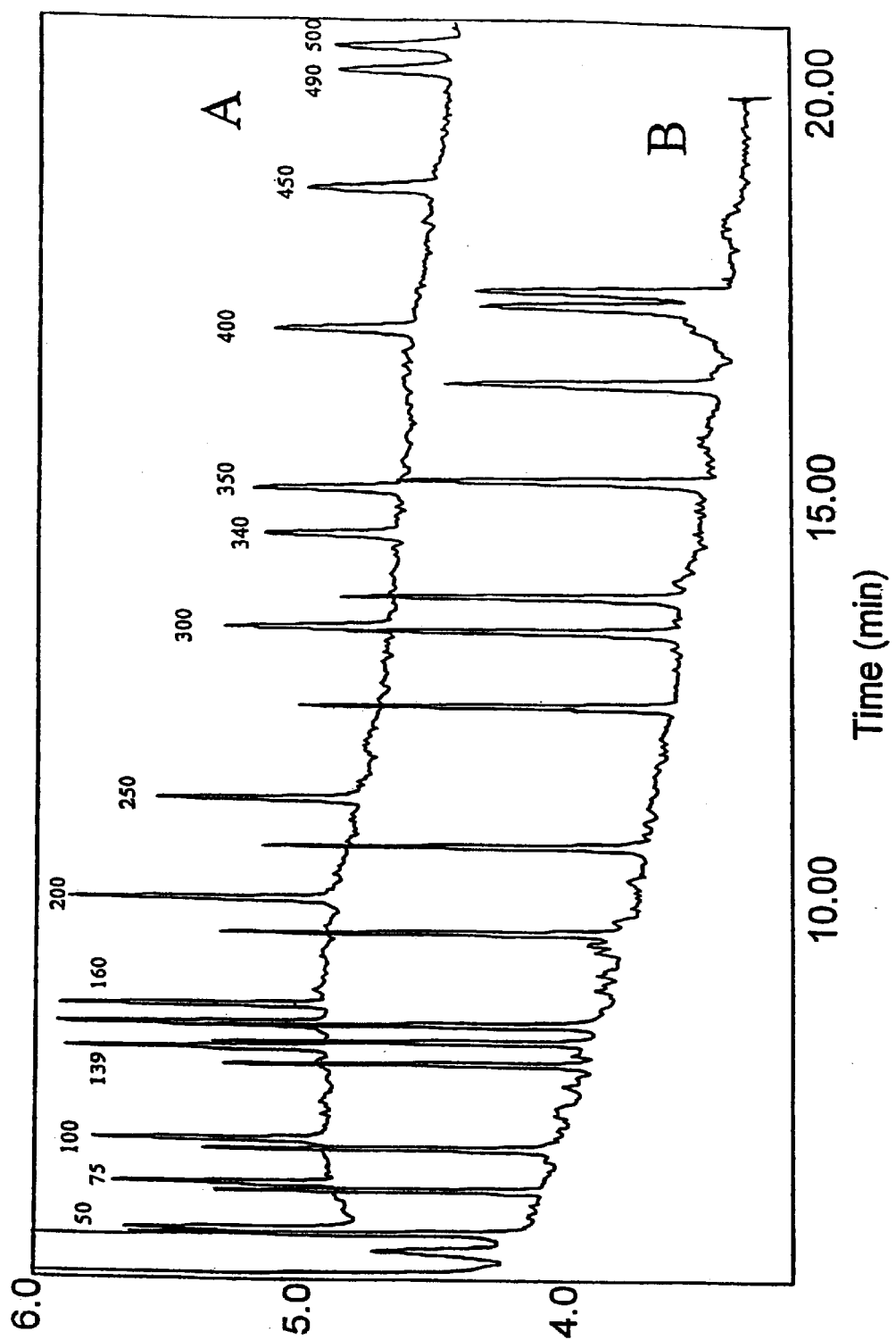
FIG. 2 provides results of electrophoretic separation of a single-stranded DNA ladder in an untreated polymethylmethacrylate capillary and a coated fused silica capillary.

Results are presented in FIG. 2. In the plots, the separation of GeneScan 500 fragments in acrylic polymer capillary (trace A) is overlaid with the results obtained using an identical sample and separation conditions in a coated fused silica capillary of the same I.D. and length (trace B). The separation in acrylic polymer capillaries shows baseline separation for all the fragments, except for the 35 base fragment, which co-migrated with the primer peak in the front of the electropherograms. Retention time differences are related to differences in electroosmotic flow in the capillary surfaces.

Example 3

CE of the Fragments in the HAE III Digest of ΦX174 RF DNA in a Sealed Plastic PMMA/ Mylar™ Microchannel Structure Photolithographic, electroforming and injection molding techniques were used to prepare an acrylic polymer (AtoHaas, Plexiglas™V825NA-100) microchannel base plate. The microchannel structure corresponds to two crossed linear channels of dimensions 2 cm and 5.5 cm in length respectively. The channels cross-section is trapezoidal, at widest it measures 120 µm and at narrowest 30 µm, with an average depth of 40 µm. At the termini of the channels, holes of 3 mm in diameter were drilled as buffer reservoirs. The channels were covered by thermal lamination of a 2 mil thick sheet of Mylar™ coated with a thermally-activated adhesive (MonoKote™, made by Top Flight Co.) at 105° C. for 5 minutes. Electrodes of 76 micron diameter platinum wire were routed to each of the four reservoirs and terminated at one edge of the chip with a 4-prong 2.54 mm pitch KK® electrical heater (Waldon Electronics). No pretreatment or coating procedure was applied to the walls of the microchannel. The separation microchannel formed this way has three acrylic limiting walls and a fourth wall surface of the MonoKote adhesive.

Figure 3:
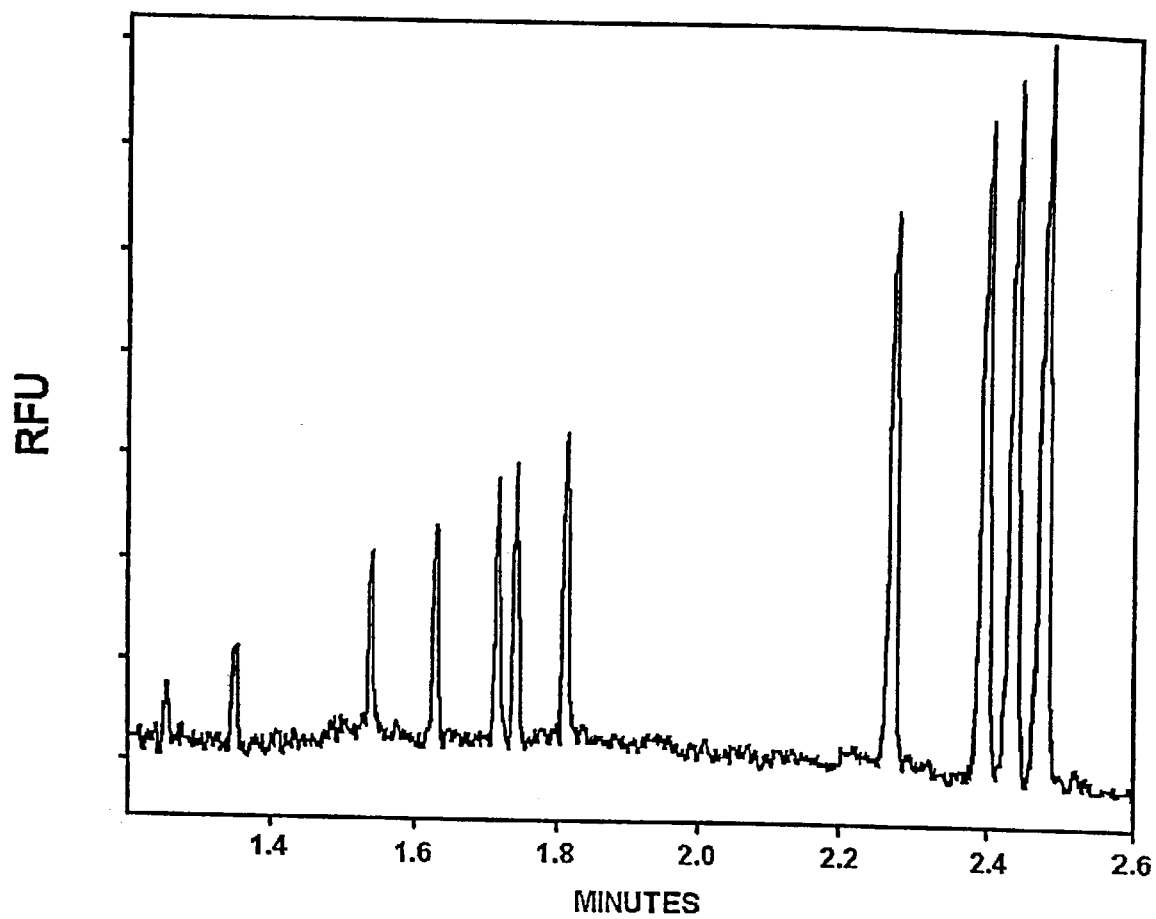
FIG. 3 provides results of electrophoretic separation of fragments in the HAE III digest of ΦX174 RF DNA in a sealed plastic PMMA/Mylar™ microchannel structure.

DNA separations were done in a sieving matrix consisting of 0.5% (w/v) hydroxyethylcellulose (HEC, MW 90,0000–105,0000), dissolved in 0.5× TBE with 2.5 µg/mL ethidium bromide. A sample of Hae 111 digest of ΦX174 RF DNA with fragments ranging in size 72 to 1354 base pairs previously diluted in run buffer was injected in the separation microchannel. After sample injection, separation of double stranded fragments was performed at an effective field strength of 190 V/cm. Fragment detection was performed through the PMMA base plate, using a fluorescence microscope (Olympus America) with photometer detection system (Photon Technology International). Excitation was derived from a deuterium lamp and delivered to the separation channel through a dichroic cube with 530 nm excitation filter, a 560–580 nm dichroic mirror, and a 590 nm long pass emission filter. Representative results of this separation are shown in FIG. 3 for an effective separation length of 4 cm with a total separation time of 2.6 minutes.

Example 4

CE of the Fragments in the HAE III Digest of ΦDX174 RF DNA in a Sealed Plastic PMMA/ PDMS Microchannel Structure In this Example, a microchannel base plate was formed as described in Example 3. The channels were covered with a film composite of polyethylene (PE) and polydimethylsiloxane (PDMS) elastomeric material. The cover film was prepared by applying a thin coat (about 100 µm) of Sylgard 184 (PDMS, Dow Corning) to a 2 mil polyethylene film (Barrier Films). The elastomeric layer of PDMS was pre-cured for 30 minutes in air at room temperature. The pre-cured PE/PDMS composite was applied to the PMMA channel base plate and allowed to cure for 24 hours at room temperature. No pretreatment or coating procedure was applied to the walls of the microchannel. The separation microchannel formed this way has three acrylic limiting walls and a fourth wall surface of the PDMS elastomeric material.

Figure 4:
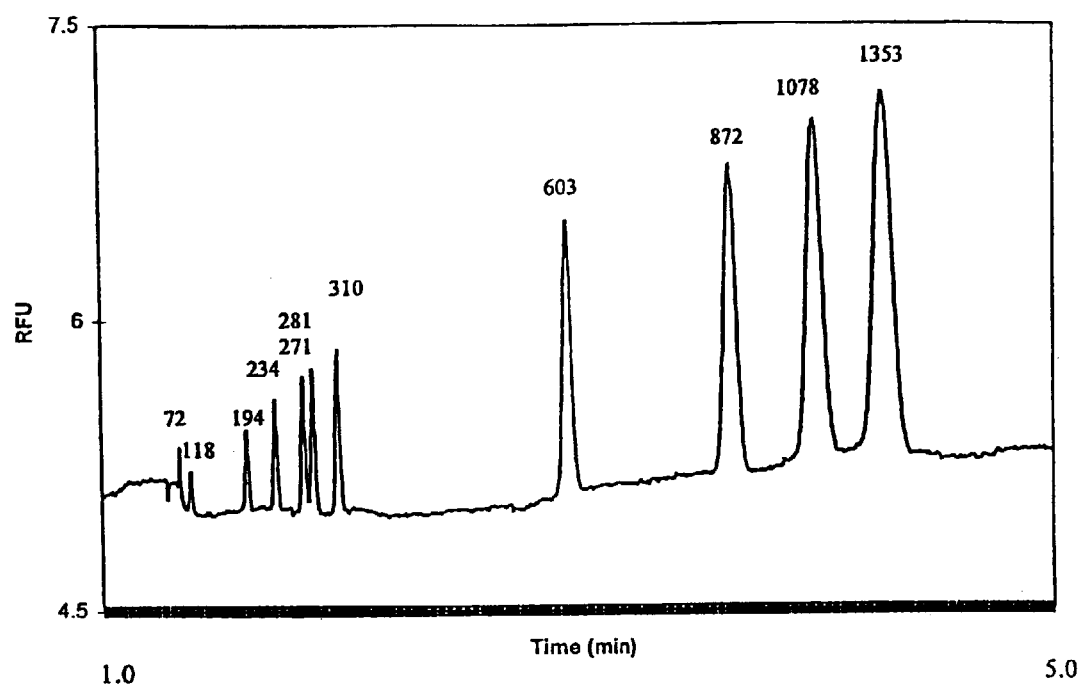
FIG. 4 provides results of electrophoretic separation of fragments in the HAE III digest of ΦX174 RF DNA in a sealed plastic PMMA/PDMS microchannel structure.

The experimental parameters and conditions for the electrophoresis separation and detection of the Hae III digest of ΦX174 RF DNA fragments under non-denaturing conditions were as in Example 3. Results of the separation using the PMMA/PDMS microchannel structures are shown in FIG. 4. In this Example, separation of the eleven double stranded fragments was achieved in 5.0 minutes of total separation time.

Example 5

Separation of Single Stranded DNA Fragments Under Denaturant Conditions in PMMA/PMMA Microchannel Structures For this example, PMMA/PMMA microchannel structures were prepared using an injection molded microchannel base plate prepared generally as described in Examples 2 and 3. A flat PMMA plate injection molded using the same procedure was used as the cover plate to enclose the microchannel structure. Physical bonding between the base and cover plates was achieved using a thermobonding procedure carried out generally as follows. The microchannel base plate and the flat cover plate were mounted together in a mechanical fixture that allows plate heating and mechanical encasing of the two plates under pressure. For bonding, the fixture containing the microchannel cassette structure was heated to 104° C. at a rate of 1° C./min in an oven. The temperature was then maintained 104° C. for 2 hours. During this time, the two plate surfaces meltd and fused to each other. To complete the bonding, the temperature was reduced to room temperature at a rate of 1° C./min. Then the fixture was opened and the PMMA/PMMA microchannel structure was removed. In the resulting microchannel containing cassettes, the channels are limited by four acrylic walls produced from the same acrylic injection molding resin. The walls are well-bonded, allowing the loading of viscous solutions under 100–200 psi pressure using a syringe adapted into the well opening of the microchannel.

Figure 5:
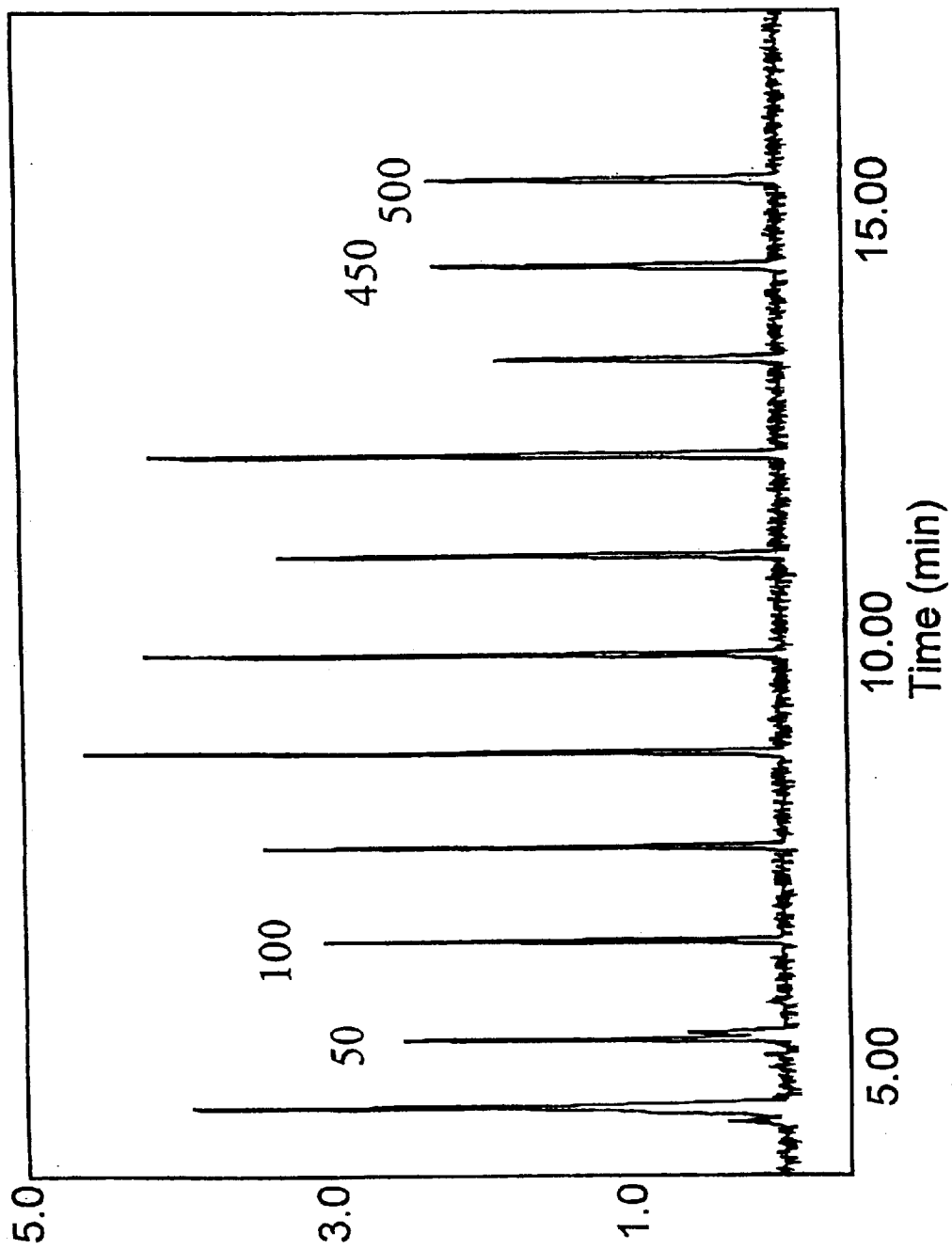
FIG. 5 provides results of electrophoretic separation of single stranded DNA fragments having sizes from 50 to 500 bases at 50-base intervals in a thermobonded PMMA/PMMA microchannel structure.

As a demonstration of the separation of single stranded DNA fragments in such a thermobonded PMMA/PMMA structure, sieving gels were prepared as a solution of a linear polymer (4.5% by wt, MW=$3\times10^6$) in 7 M urea and 1× TBE buffer. The separated fragments of DNA correspond to a CyS (indodicarbocyanine dye amidite, Biological Detection Systems, Inc.) labeled DNA Size Marker of single-stranded fragments ranging in size from 50 to 500 bases, separated by exactly 50 bases (Pharmacia). Electrophoresis was performed at 150 V/cm, with an effective channel length of 4 cm for 16 minutes. Detection was achieved using confocal fluorescence detection with He/Ne laser excitation (EX:633 nm) and emission at 670 nm. FIG. 5 provides an example of the electrophoretic separation of single stranded DNA fragments obtained under these experimental conditions.

Example 6

Chemical Bonding of Acrylic Base Plates to an Acrylic Flat Cover and Film Forming Materials In these Examples, microchannel structures are made by chemically bonding acrylic base plates to acrylic flat cover of film-forming materials.

Example 6A: In this example, a chemical bonding material is prepared as a mixture of linear low molecular weight polymethylmethacrylate (MW=$10^5$–$10^6$, 5–30% w/w) in methylmethacrylate monomer (70–95% w/w) and a thermal polymerization initiator (i.e.: t-butylperoxypivalate, tBPP, Lupersol 1 1-Pennwalt). Using spin coating tools, a thin layer (1–10 μm) of this bonding material is applied to a flat cover plate made of polymethylmethacrylate (PMMA). The base plate is aligned and firmly positioned over the cover plate to form a base-to-cover sandwich, and pressure is applied (50–150 psi) to maintain the contact of base-to-cover. The assembly of base-to-cover is carried out in a manner that avoids overflow of the channels with the bonding material. The bonding process is completed by curing the acrylic interface at 70° C. for 1–2 hours.

In a similar process, a cover film of 50–500 μm thickness can be substituted for the cover plate. Films made of hydrocarbon based polymers (e.g., low density polyethylene, amorphous polypropylene), fluorinated polymers (e.g., polytetrafluoroethylene), or copolymers or blends of such polymers are suitable for this process and provide added optical transparency required for spectroscopic (fluorescence and UV) detection. Chemical bonding of the acrylic base to the cover film is carried out generally as described above for the acrylic flat cover. In this format, the application of the bonding material to the cover film can be carried out manually, for example using a fine paint brush or rollers, or automatically, for example using roll coaters or float coaters.

Example 6B: In this example, the bonding material is prepared as a blend of linear low molecular weight polymethylmethacrylate (MW=$10^5$–$10^6$, 5–30% w/w) dissolved in a mixture of methylmethacrylate monomer (60–95% w/w), allylmethacrylate (1–5% w/w), and 0.5% w/w 2-hydroxy-2,2-dimethylactophenone (Darocure-1173, EM Industries) as a polymerization photoinitiator. Using spin coating tools, a thin layer (1–10 μm) of this bonding material is applied to the flat cover plate made of polymethylmethacrylate (PMMA). The coated cover is exposed for 10–30 seconds to a 15 watt fluorescent lamp at 1 inch from the surface. With this pre-curing step, the thin film has a non-flowable consistency, tacky toward the surface of a PMMA base plate with microchannel structures. The base plate is aligned and firmly positioned over the cover plate to form a base-to-cover sandwich, and 50–150 psi of pressure is applied to maintain the contact of base-to-cover and complete the bonding process by curing the acrylic interface under a 15 watt fluorescent lamp at 1 inch from the surface for 1–2 hours. The final cured interface provides a crosslinked, optically transparent cement between the cover and base plates, with good wall contact to the cover plate and open channels for analytical applications.

It is evident from the above results and discussion that the acrylic polymer microchannels according to the subject invention provide a viable alternative to microchannels prepared from fused silica in electrophoretic applications. The unmodified acrylic microchannels according to the subject invention give rise to EOF of sufficiently small magnitude so as to provide for good resolution of electrophoretically separated components, similar to the separation and resolution achieved with coated fused silica channels. As the subject microchannels require no surface modification, they are easier to prepare and use than surface modified channels. Furthermore, the optical transparency of the acrylic polymer material of the subject channels makes them amenable for use with on-line detection techniques. The subject microchannels are particularly suited for the separation of complex mixtures of large numbers of differently sized nucleic acids, such as labeled DNA fragments generated in genome sequencing applications.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An enclosed microchannel device for use in a method where charged entities are moved through a network of interconnected microchannels under the influence of applied electric fields, the said device comprising a moldable polymeric base member, cover member,. and means for bonding together the base and cover members;

said base member having at least one substantially planar acrylic surface and a network of interconnected microchannels having cross-sectional dimensions ranging from about 1 μm to 200 μm provided in said acrylic surface, and adapted to receive charged entities for movement under the influence of said applied electric fields;

said cover member comprising a substantially planar and optically-transparent thin polymeric cover film approximately 1 to 2 mils thick having at least one substantially planar surface;

said base and cover members bonded together by the steps of applying an optically transparent bonding material to at least one of said planar surfaces, partially curing the bonding material, apposing said planar surfaces of said cover member and said base member, and curing said bonding material to form a stable and optically transparent interface between said planar surfaces.

2. The device according to claim 1, wherein said base and cover members comprise a polymethylmethacrylate.

3. The device of claim 1 wherein said applying step comprises applying the bonding material to said surface in a flowable state and wherein said partially curing step comprise partially curing the bonding material to a non-flowable state.

4. The device of claim 1 wherein said bonding material further comprises a polymerization initiator.

5. The device of claim 4 wherein said polymerization initiator comprises a photoinitiator and wherein said apposing step includes the step comprises exposing said bonding material between said apposed surfaces to light at a wavelength and intensity and for a time sufficient to cause polymerization.

6. The device of claim 4 wherein said polymerization initiator comprises a thermal initiator and wherein said apposing step comprises heating said bonding material between said apposed surfaces to a temperature and for a time sufficient to cause polymerization.

7. The device according to claim 1, wherein said device comprises a means for on-line optical detection.

* * * * *